(12) United States Patent
Higuchi et al.

(10) Patent No.: US 10,085,803 B2
(45) Date of Patent: Oct. 2, 2018

(54) STERILE DRAPE

(71) Applicant: Sony Olympus Medical Solutions Inc., Tokyo (JP)

(72) Inventors: Gakuji Higuchi, Tokyo (JP); Junichi Nozawa, Tokyo (JP); Tomonori Ishikawa, Tokyo (JP); Masataka Kado, Kanagawa (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 6 days.

(21) Appl. No.: 14/732,137

(22) Filed: Jun. 5, 2015

(65) Prior Publication Data
US 2015/0366618 A1 Dec. 24, 2015

(30) Foreign Application Priority Data

Jun. 20, 2014 (JP) ................ 2014-127685

(51) Int. Cl.
| *A61B 19/08* | (2006.01) |
| *A61B 19/00* | (2006.01) |
| *A61B 90/50* | (2016.01) |
| *A61B 46/10* | (2016.01) |
| *A61B 90/20* | (2016.01) |

(52) U.S. Cl.
CPC ............ *A61B 19/081* (2013.01); *A61B 46/10* (2016.02); *A61B 90/50* (2016.02); *A61B 90/20* (2016.02)

(58) Field of Classification Search
CPC ....... A61B 19/00; A61B 19/08; A61B 19/081; A61B 19/26; A61B 19/20; A61B 19/50;
(Continued)

(56) References Cited

U.S. PATENT DOCUMENTS 3,528,720 A * 9/1970 Treace ................... A61B 46/10
206/305
3,698,791 A 10/1972 Walchle et al.
(Continued)

FOREIGN PATENT DOCUMENTS

| JP | 5-173053 A | 7/1993 |
| JP | 8-191842 | 7/1996 |

(Continued)

OTHER PUBLICATIONS

Extended European Search Report dated Aug. 21, 2015 in Patent Application No. 15170839.3.
Office Action dated Apr. 3, 2018, in Japanese Patent Application No. 2014-127685 (5 pages).

*Primary Examiner* — Jie Lei
(74) *Attorney, Agent, or Firm* — Oblon, McClelland, Maier & Neustadt, L.L.P.

(57) ABSTRACT

Provided is a sterile drape configured to cover a medical observation apparatus to keep the medical observation apparatus sterile, the medical observation apparatus including a microscope part configured to magnify and image a microfine site of an observation object, an input part configured to receive an input of an operation instruction to the microscope part, and a grip part having a bar shape and having a surface provided with at least a portion of the input part, the sterile drape including: an attaching part configured to be fixed and attached to the grip part in a state where the sterile drape covers the medical observation apparatus.

10 Claims, 13 Drawing Sheets

(58) Field of Classification Search
CPC ..... A61B 1/05; A61B 1/0052; A61B 1/00142; A61B 1/06; A61B 1/121; A61B 46/10; A61B 90/20; A61B 90/50; G02B 7/1815; G02B 7/28; G02B 5/124; G02B 23/16; B60R 1/0602
USPC ....... 359/510, 507, 508, 511, 512, 513, 514; 600/249, 122, 133, 109, 131
See application file for complete search history.

(56) References Cited

U.S. PATENT DOCUMENTS

| | | | |
|---|---|---|---|
| 4,799,779 A * | 1/1989 | Mesmer | A61B 46/10 206/305 |
| 5,231,279 A * | 7/1993 | Nakamura | G02B 21/241 250/201.2 |
| 5,803,905 A | 9/1998 | Allred et al. | |
| 5,873,814 A | 2/1999 | Adair | |

FOREIGN PATENT DOCUMENTS

| | | |
|---|---|---|
| JP | 10-90609 | 4/1998 |
| JP | 3704381 B2 | 10/2005 |
| JP | 2010-512851 | 4/2010 |
| JP | 2012-205895 | 10/2012 |
| JP | 2013-103059 | 5/2013 |
| WO | WO 98/02107 A1 | 1/1998 |

* cited by examiner

STERILE DRAPE

CROSS REFERENCE TO RELATED APPLICATIONS

This application claims the benefit of Japanese Priority Patent Application JP 2014-127685 filed Jun. 20, 2014, the entire contents of which are incorporated herein by reference.

BACKGROUND

The present disclosure relates to a sterile drape configured to be applied to a medical observation apparatus for observing a microfine site of an observation object.

In the past, as a medical observation apparatus for observing a microfine site in the brain, heart or the like of a patient, being an observation object, there have been known a surgery microscope including a microscope part and an arm movably supporting the microscope part (see JP H5-173053B, for example). To move the microscope part of this surgery microscope, the user moves the arm to a desired position while pressing down the arm operation switch provided to the grip part of the arm.

When a surgery is performed on a patient by using a medical observation apparatus such as a surgery microscope, a sterile drape is used in order to keep the surfaces of the medical observation apparatus sterile (see U.S. Pat. No. 3,698,791B and JP 3704381B, for example). The sterile drape, a bag-shaped member formed of a material such as vinyl, is applied to cover the medical observation apparatus.

SUMMARY

Now, in JP H5-173053B, the grip part is provided with the input part configured to receive an input of an operation instruction to the microscope part. In such a case, when applied to this grip part, the sterile drape is prone to slip on the grip part while the user grips the grip part. This carries the risk of making it difficult for the user to carry out switch inputs as the user wishes, and thus of impairing the operability of the grip part.

According to an embodiment of the present disclosure, there is provided a sterile drape capable of satisfactorily maintaining the operability of the grip part provided with an operation input part in the medical observation apparatus to which the sterile drape is applied.

According to an embodiment of the present disclosure, there is provided a sterile drape configured to cover a medical observation apparatus to keep the medical observation apparatus sterile, the medical observation apparatus including a microscope part configured to magnify and image a microfine site of an observation object, an input part configured to receive an input of an operation instruction to the microscope part, and a grip part having a bar shape and having a surface provided with at least a portion of the input part, the sterile drape including: an attaching part configured to be fixed and attached to the grip part in a state where the sterile drape covers the medical observation apparatus.

A surface of the attaching part may have a shape protruding with respect to the grip part, the surface not facing the medical observation apparatus in the state where the sterile drape covers the medical observation apparatus.

An input-part cover formed of an elastic member and configured to cover the at least a portion of the input part provided to the grip part in the state where the sterile drape covers the medical observation apparatus may be further included.

The microscope part of the medical observation apparatus may have a pillar shape to function as the grip part. The attaching part may be configured to be attached to the microscope part.

The attaching part may have a shape finable to a surface of the grip part.

The attaching part may have a band shape, and include engaging parts respectively on both end portions in a band length direction in a manner that one of the end portions is engaged with the other end portion.

The attaching part may be formed of an elastic member.

The attaching part may be formed of an elastic member having a tubular shape whose diameter is smaller than an outer diameter of the microscope part.

The attaching part may include a tubular part formed of an elastic member having a tubular shape whose diameter is smaller than an outer diameter of the microscope part, and a cover glass provided to an end part of the tubular part in a height direction of the tubular part, and configured to protect an opening surface through which the microscope part condenses light from the observation object, the end part corresponding to a front end of the microscope part.

The tubular part may have a flange portion protruding in a radial direction at an outer periphery portion of the cover glass.

The attaching part may be provided with a slit formed by cutting from an end, from which the microscope part is inserted, of the attaching part.

The microscope part of the medical observation apparatus may have a pillar shape to function as the grip part. The medical observation apparatus may further include a support part having at least one set of two arm parts and a joint part that rotatably connects one of the two arm parts to the other, and supporting the microscope part at a front end part rotatably around an axis in a height direction of the microscope part, and an arm operation switch provided to a side surface of the microscope part, and configured to receive an operation input for allowing rotations of the arm parts, the side surface corresponding to an upper side of an image based on an imaging signal. The input part may include the arm operation switch.

According to one or more of embodiments of the present disclosure, a sterile drape includes an attaching part configured to be fixed and attached to a grip part in a state where the sterile drape covers a medical observation apparatus. Accordingly in the observation apparatus to which the sterile drape is applied, the operability of the grip part provided with an operation input part can be satisfactorily maintained.

DETAILED DESCRIPTION OF THE EMBODIMENTS

Hereinafter, modes (hereinafter referred to as "embodiments") for carrying out the present disclosure will be described with reference to the drawings. Note that the drawings are only schematic representations, where some parts might have dimensional relationships or proportions different from one drawing to another.

Embodiment 1

Figure 1:
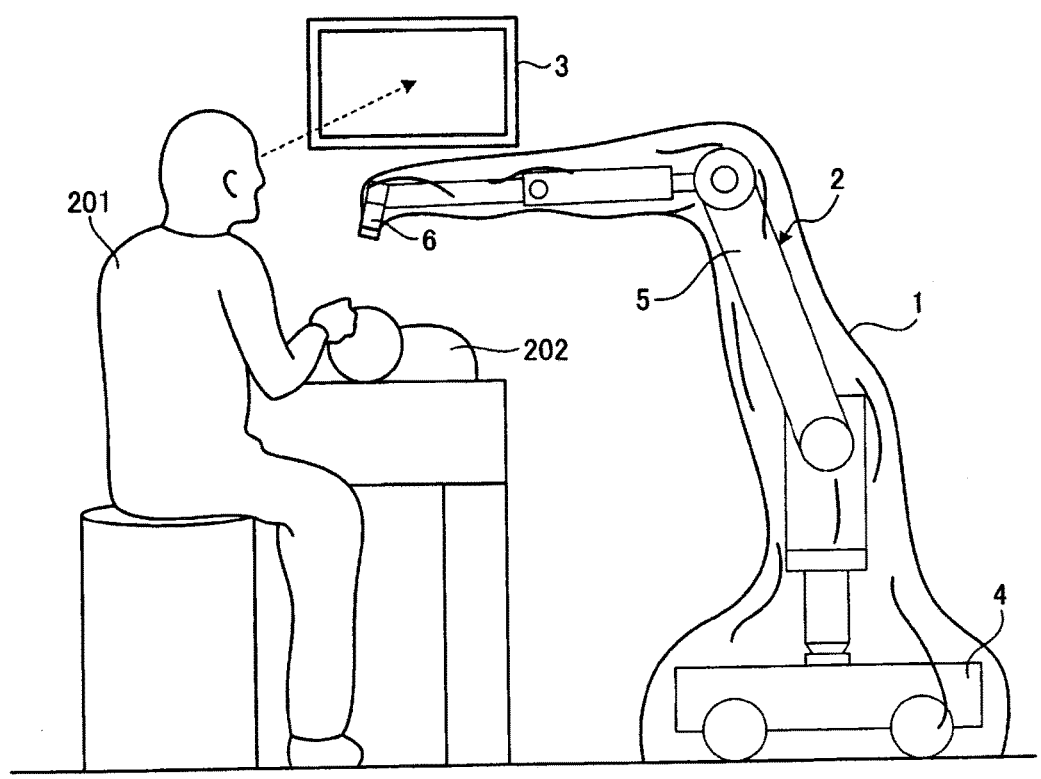
FIG. 1 shows a configuration and a usage mode of a sterile drape according to an embodiment 1 of the present disclosure.

FIG. 1 shows a configuration and a usage mode of a sterile drape according to an embodiment 1 of the present disclosure. Applied to cover a medical observation apparatus (hereinafter referred to as observation apparatus) 2, which functions as a microscope configured to magnify and image the microstructure of an observation object, the sterile drape 1 shown in FIG. 1 keeps the surfaces of the observation apparatus 2 sterile. The main body of the sterile drape 1 is formed of a material such as vinyl, and has an atypical bag shape conforming to the shape of the observation apparatus 2.

FIG. 1 shows a situation where a surgeon 201 is performing a surgery on a patient 202. In FIG. 1, a display 3 displays a magnified image of a surgery site of the patient 202 imaged by the observation apparatus 2. The surgeon 201 is performing the surgery while watching the magnified image of the surgery site of the patient 202 displayed on the display 3.

The observation apparatus 2 includes: a base part 4 configured movable on a floor surface; a support part 5 having multiple sets of two arm parts and a joint part that rotatably connects one of the two arm parts to the other, and supported by the base part 4; and a microscope part 6 having a cylindrical pillar shape, provided to the front end of the support part 5 and configured to magnify and image a microfine site of an observation object.

Figure 2:
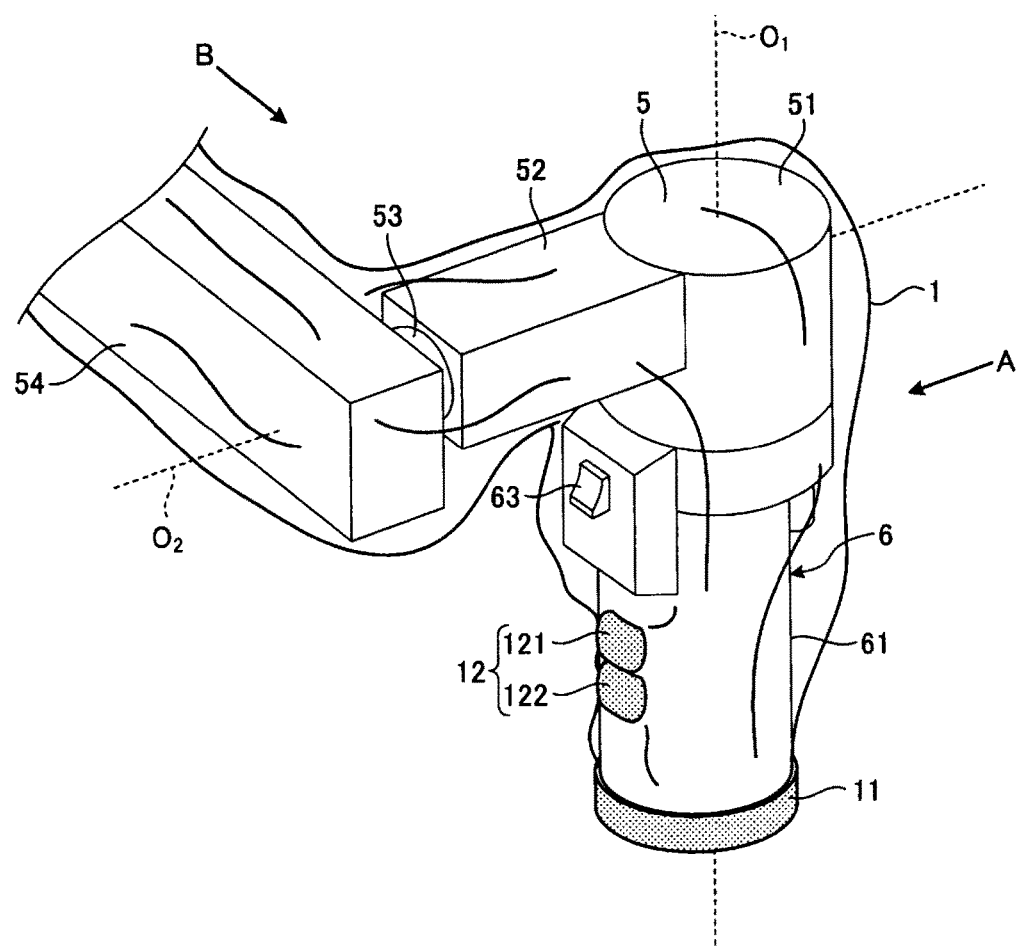
FIG. 2 is an enlarged perspective view showing a configuration of a substantial part of the sterile drape according to the embodiment 1 of the present disclosure, and a configuration of a part, to which the substantial part is applied, of a medical observation apparatus.

FIG. 2 is an enlarged perspective view showing a configuration of a substantial part, which is applied to a front end part of the observation apparatus 2, of the sterile drape 1, and a configuration of the support part 5 and the microscope part 6 in the front end part of the observation apparatus 2.

Firstly, description will be given of a configuration of a front end part of the support part 5. The support part 5 includes: a first joint part 51 rotatably supporting the microscope part 6 at the front end; a first arm part 52 fixed to the first joint part 51 and extending from the side surface of the first joint part 51; a second joint part 53 rotatably holding the first arm part 52 at the front end; and a second arm part 54 whose front end is fixed to the second joint part 53.

The first joint part 51, having a cylindrical shape, holds the microscope part 6 rotatably around a first axis $O_1$, which is the central axis in the height direction of the first joint part 51.

The first arm part 52 has a shape extending from the side surface of the first joint part 51 in the direction perpendicular to the first axis $O_1$.

The second joint part 53, having a cylindrical shape, holds the first arm part 52 rotatably around a second axis $O_2$, which is the central axis in the height direction of the second joint part 53 and is perpendicular to the first axis $O_1$.

The second arm part 54 has a shape extending in the direction perpendicular to the second axis $O_2$.

In the portion between the base end side of the second arm part 54 and the base part 4, the support part 5 is provided with multiple joint parts and arm parts (see FIG. 1). Note that the support part 5 have only to have at least one set of two arm parts and a joint part that rotatably connects one of the two arm parts to the other. Thus, the configuration of the portion between the base end side of the second arm part 54 and the base part 4 may be changed as appropriate.

The first and second joint parts 51 and 53 have electromagnetic brakes configured to inhibit the rotations of the microscope part 6 and the first arm part 52, respectively. The electromagnetic brakes are released while an arm operation switch 63 (described later) provided to the microscope part 6 is pressed down, thus allowing the rotations of the microscope part 6 and the first arm part 52. Note that air brakes may be employed instead of the electromagnetic brakes.

In the support part 5, there is formed a hollow space that can accommodate multiple cables. This prevents the cables from being exposed outside of the observation apparatus 2, and thus from catching a person or a thing. In addition, the observation apparatus 2 can be downsized as compared to the case where the multiple cables are laid outside the main body, and also prevents the cables from hindering the vision of the surgeon 201.

Figure 3:
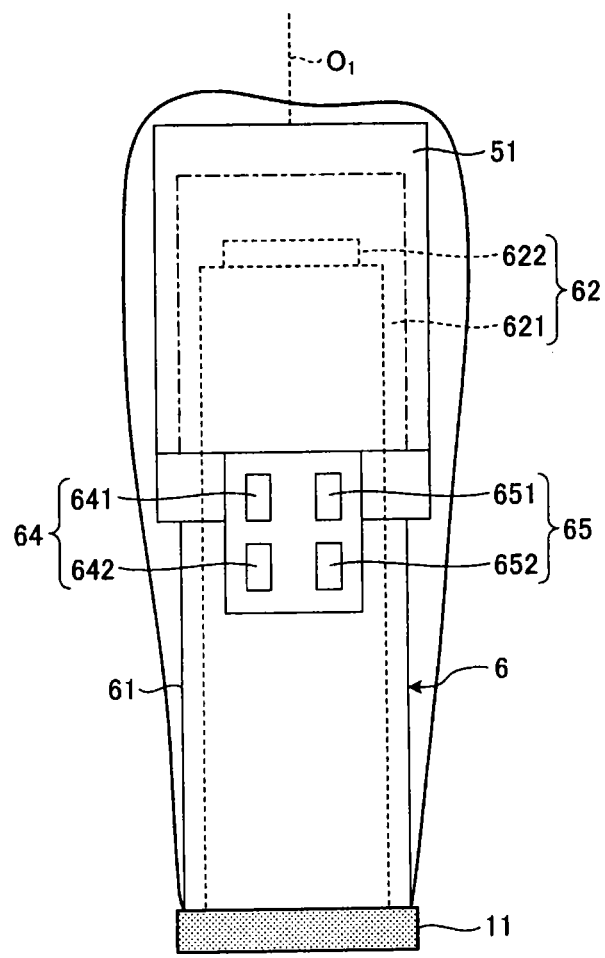
FIG. 3 is a side view seen from the direction of the arrow A of FIG. 2.

Next, description will be given of a configuration of the microscope part 6. FIG. 3 is a side view seen from the direction (direction parallel to the second axis $O_2$) of the arrow A of FIG. 2. The microscope part 6 includes: a tubular part 61 having a cylindrical shape; an imaging part 62 provided to the hollow space of the tubular part 61, and configured to magnify and image an image of the observation object; the arm operation switch 63 configured to receive an operation input for releasing the electromagnetic brakes of the first and second joint parts 51 and 53 so as to allow the rotations of these joint parts; magnification changing switches 64 configured to receive an operation input for changing imaging magnification of the imaging part 62; and focal-distance changing switches 65 configured to receive an operation input for changing the focal distance to the observation object.

The tubular part 61 has a cylindrical shape whose diameter is smaller than that of the first joint part 51, and, at its lower end part, has an opening surface provided with a cover glass (not shown) for protecting the imaging part 62. Note that the shape of the tubular part 61 is not limited to cylindrical but may be polygonal tubular.

The imaging part 62 includes: an optical system 621 that has multiple lenses arranged so that the optical axes thereof may be aligned with the first axis $O_1$, and that is configured to condense light from the observation object to form an image thereof; and an image sensor 622 configured to receive the light condensed by the optical system 621, and to photoelectrically convert the light to generate imaging signals.

The optical system 621, having the multiple lenses, is capable of changing magnification of an image of the observation object in response to the operation of the magnification changing switches 64, and of changing the focal distance to the observation object in response to the operation of the focal-distance changing switches 65.

The image sensor 622 is formed of a charge coupled device (CCD) or a complementary metal oxide semiconductor (CMOS). The imaging signals outputted by the image sensor 622 are transmitted, through the transmission cables provided in the internal hollow space of the support part 5, to an image generating device (not shown) configured to generate image data for display.

The imaging part 62 is inserted into the inside of the first joint part 51. In FIG. 3, the optical system 621 and the image sensor 622 placed in the hollow spaces of the tubular part 61 and the first joint part 51 are schematically shown in broken line. Also in FIG. 3, a portion inserted into the inside of the first joint part 51 of the microscope part 6 is schematically shown in dashed-dotted line. The portion rotates together with the tubular part 61 with respect to the first joint part 51.

The arm operation switch 63 is a push-button switch. While the surgeon 201 is pressing down the arm operation switch 63, the electromagnetic brakes of the first and second joint parts 51 and 53 are released. The surgeon 201 operates the microscope part 6 while facing a portion, provided with the magnification changing switches 64 and the focal-distance changing switches 65, of the side surface of the tubular part 61.

The magnification changing switches 64 include a zoom-in switch 641 for increasing magnification and a zoom-out switch 642 for decreasing magnification.

The focal-distance changing switches 65 include a distant-view focus switch 651 for increasing the focal distance to the observation object, and a near-view focus switch 652 for decreasing the focal distance to the observation object.

The microscope part 6 having the configuration as described above also functions as a grip part gripped by the surgeon 201 operating the microscope part 6 to shift the viewing area thereof.

Next, description will be given of a configuration of the part, which is applied to the front end part of the observation apparatus 2, of the sterile drape 1. As shown in FIG. 2, the sterile drape 1 includes an opening cover 11 and an attaching part 12. The opening cover 11, having a cylindrical shape, is attached to the front end of the tubular part 61 of the microscope part 6, and provided with a cover glass (not shown) for protecting the opening surface through which the microscope part 6 condenses light from the observation object. The attaching part 12 is fixed and attached to a portion, located farther from the first joint part 51 than the arm operation switch 63 in the height direction of the tubular part 61, of the side surface of the tubular part 61.

Figure 4:
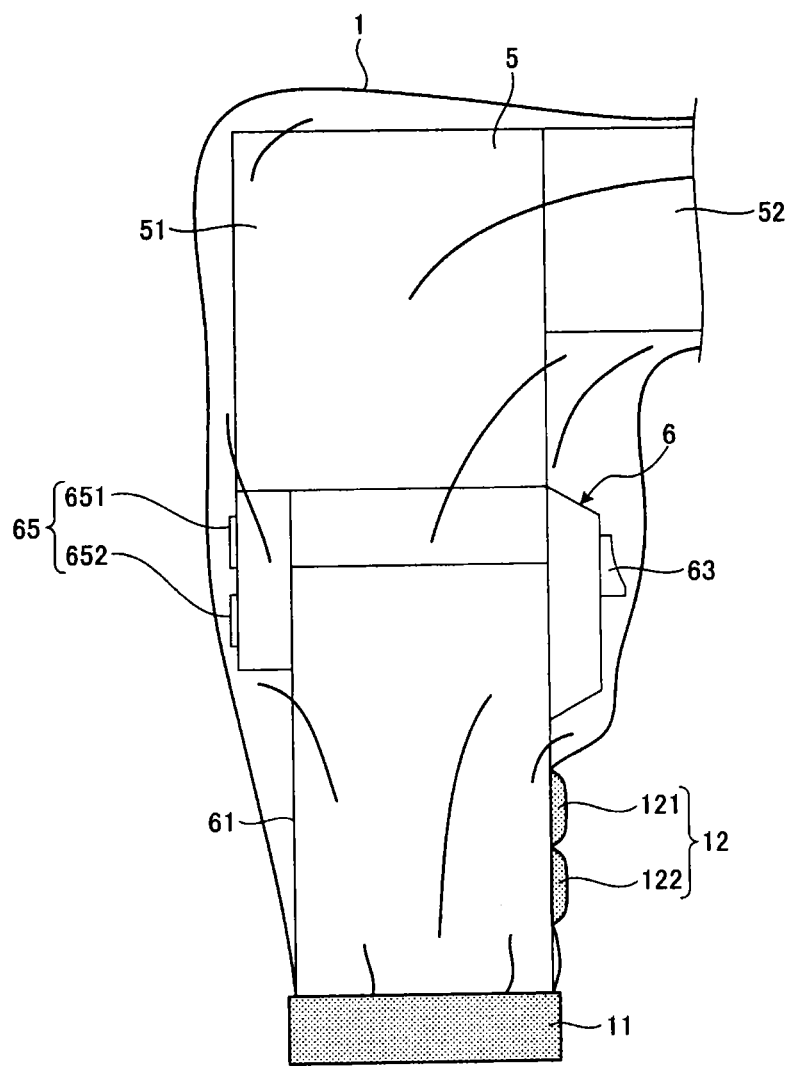
FIG. 4 is a side view seen from the direction of the arrow B of FIG. 2.

FIG. 4 is a side view seen from the direction (direction perpendicular to the first and second axes $O_1$ and $O_2$) of the arrow B of FIG. 2. The attaching part 12 includes two protrusions 121 and 122, which are provided contiguously on the outer surface of the bag-shaped main body of the sterile drape 1. When attached to the tubular part 61, the protrusions 121 and 122 are placed on the surface of the tubular part 61 so as to locate side by side in the height direction of the tubular part 61. The attaching part 12, formed of an elastic member harder than vinyl used in the main body of the sterile drape 1, is fixed and attached to the surface of the tubular part 61. The elastic member is formed of a material capable of preventing slip of an object (a hand of the surgeon 201, for example) contacting from outside. Note that the part, other than the cover glass, of the opening cover 11 is formed of a material similar to that of the attaching part 12.

Figure 5:
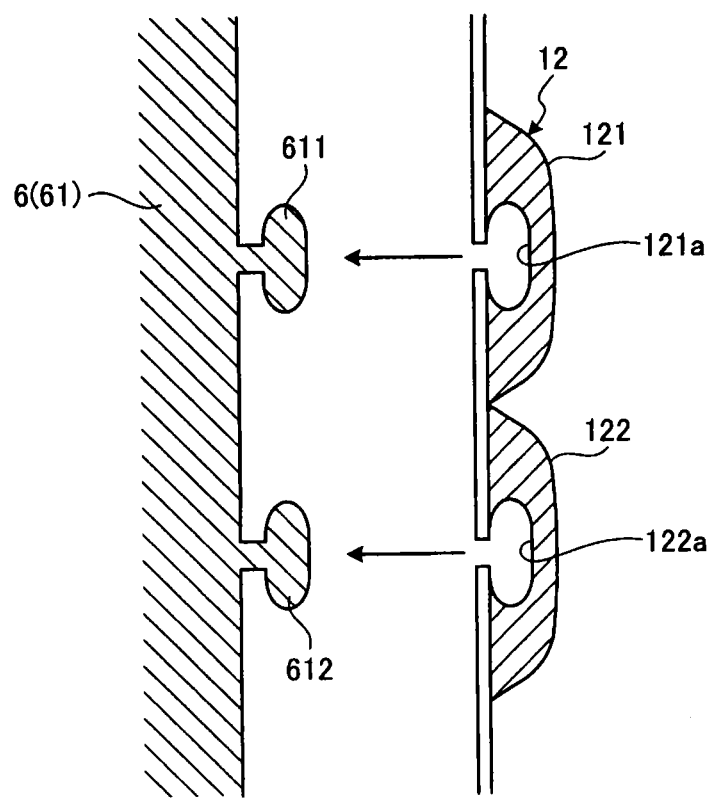
FIG. 5 schematically shows an outline of an attaching manner of an attaching part of the sterile drape according to the embodiment 1 of the present disclosure to a microscope part.

FIG. 5 schematically shows an outline of an attaching manner of the attaching part 12 to the microscope part 6 (the tubular part 61). On the back sides (sides facing the microscope part 6 when the sterile drape 1 is applied to the microscope part 6) of the protrusions 121 and 122, attaching recessed portions 121a and 122a are formed, respectively. The attaching recessed portions 121a and 122a are respectively fitted to two attaching protruding portions 611 and 612 provided side by side in the height direction (the up-down direction in FIG. 5) of the tubular part 61 on the surface of the tubular part 61. Thereby, the attaching part 12 is fixed and attached to the tubular part 61.

In applying the sterile drape 1 to cover the observation apparatus 2, the sterile drape 1 is applied to the front end part of the observation apparatus 2 by firstly attaching the opening cover 11 to the front end of the tubular part 61, and then fitting the attaching recessed portions 121a and 122a respectively to the attaching protruding portions 611 and 612.

Note that the shape of the attaching part 12 is not limited to the shape described above. Note also that, when the attaching part 12 is provided with protrusions, the number of protrusions is not limited to two as described above.

Figure 6:
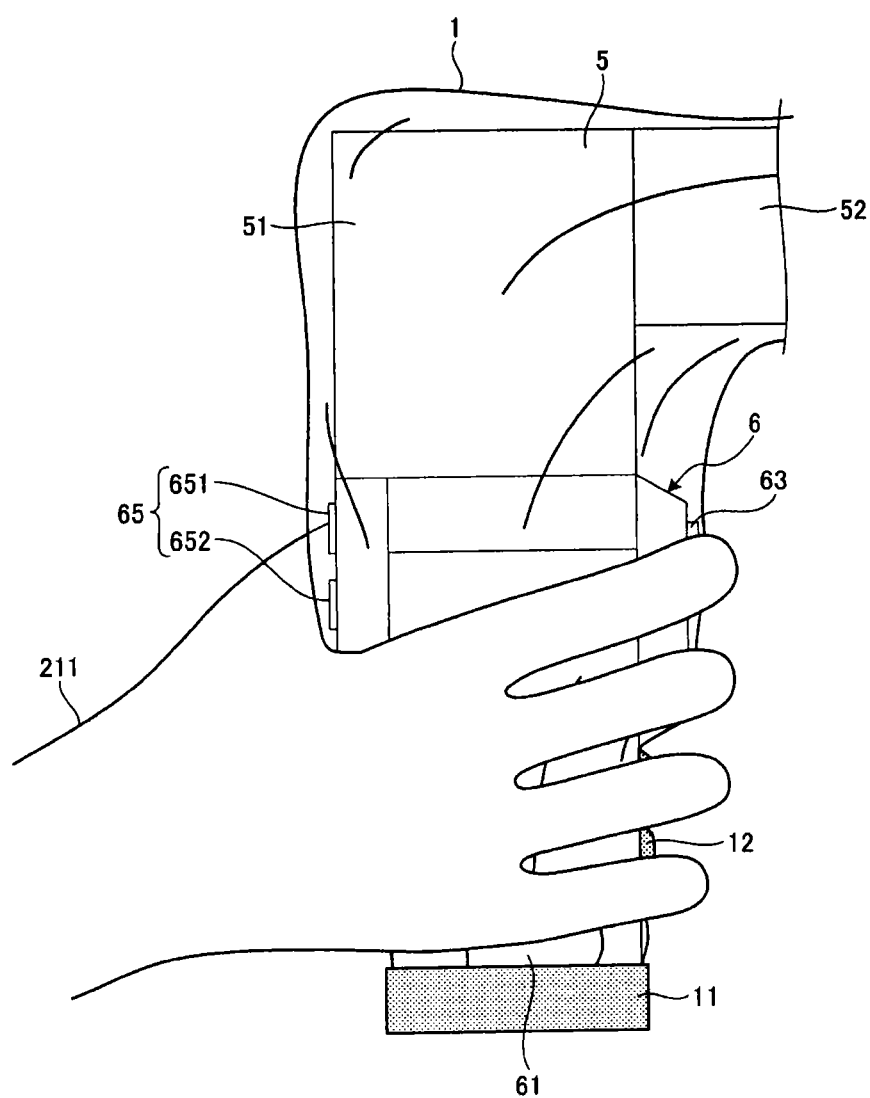
FIG. 6 schematically shows a situation where a surgeon is operating the microscope part to which the sterile drape according to the embodiment 1 of the present disclosure is applied.

FIG. 6 schematically shows a situation where the surgeon 201 is operating the microscope part 6. The surgeon 201 operates the microscope part 6 while facing the portion, provided with the magnification changing switches 64 and the focal-distance changing switches 65, of the side surface of the tubular part 61. In this event, with the microscope part 6 gripped with the right hand 211, the surgeon 201 operates the support part 5 while pressing down the arm operation switch 63 with the forefinger (or otherwise, the middle or annular finger). Accordingly, the surgeon 201 can operate the support part 5 while pressing down the arm operation switch 63 simultaneously with maintaining naturally gripping the microscope part 6.

As shown in FIG. 1, simultaneously with viewing an image (image imaged by the microscope part 6) displayed on the display 3, the surgeon 201 grips and moves the microscope part 6 to a desired position while pressing down the arm operation switch 63 of the microscope part 6. After determining where to position the viewing area of the microscope part 6, the surgeon 201 lifts the finger off the arm operation switch 63. This activates the electromagnetic brakes of the first and second joint parts 51 and 53, thus fixing the viewing area of the microscope part 6. Thereafter, the surgeon 201 performs such operations as changing the magnification by operating the magnification changing switches 64 or as adjusting the focal distance to the observation object by operating the focal-distance changing switches 65.

To make the microscope part 6 easily gripped by the surgeon 201 without hindering the vision of the surgeon 201 viewing the display 3 or the surgery site of the patient 202, it is more preferable, for example, that the tubular part 61 have an outer diameter of approximately 40 to 70 mm, and that the height from the front end of the tubular part 61 to the first joint part 51 be approximately 80 to 200 mm. In addition, it is desirable that each of the protrusions 121 and 122 of the attaching part 12 have a thickness small enough (approximately at most a few millimeters) not to impair the grippability of the tubular part 61 for the surgeon 201.

In the embodiment 1 of the present disclosure as described above, the sterile drape 1 includes the attaching part 12 configured to be fixed and attached to the microscope part 6 (grip part) in a state where the sterile drape 1 covers the observation apparatus 2. Accordingly, in the observation apparatus 2 to which the sterile drape 1 is applied, the operability of the microscope part 6 provided with the arm operation switch 63 and the like as an operation input part can be satisfactorily maintained.

In addition, in the embodiment 1, the attaching part 12 does not slip between the microscope part 6 and the vinyl body of the sterile drape 1. Thus, the user can move the microscope part 6 as the user wishes.

Moreover, in the embodiment 1, the attaching part 12 is fixed to the microscope part 6. This can minimize unnecessary looseness of the sterile drape 1 around the microscope part 6, thus preventing the sterile drape 1 from hindering the vision of the user.

Furthermore, in the embodiment 1, the attaching part 12 has a shape protruding from the outer surface of the main body. This prevents a hand of the user from slipping on the attaching part 12 while the user is moving the microscope part 6. Accordingly, the user can grip the microscope part 6 more reliably and thus can operate the microscope part 6 as the user wishes.

Note that the placing position of the attaching part 12 is not limited to the position described above. Alternatively, the attaching part 12 may be provided to the portion (portion facing the surgeon 201 performing a surgery), provided with the magnification changing switches 64 and the focal-distance changing switches 65, of the side surface of the tubular part 61, for example.

Embodiment 2

Figure 7:
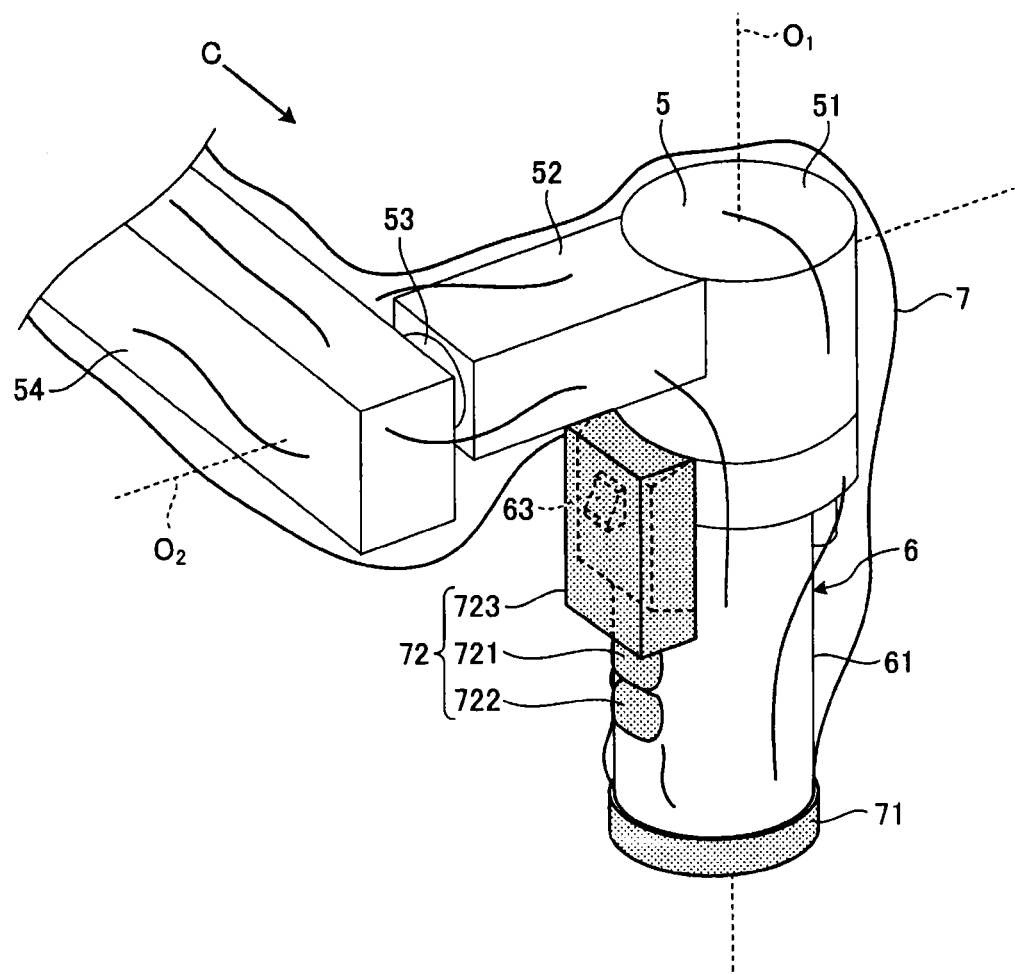
FIG. 7 is an enlarged perspective view showing a configuration of a substantial part of a sterile drape according to an embodiment 2 of the present disclosure, and a configuration of a part, to which the substantial part is applied, of a medical observation apparatus.
Figure 8:
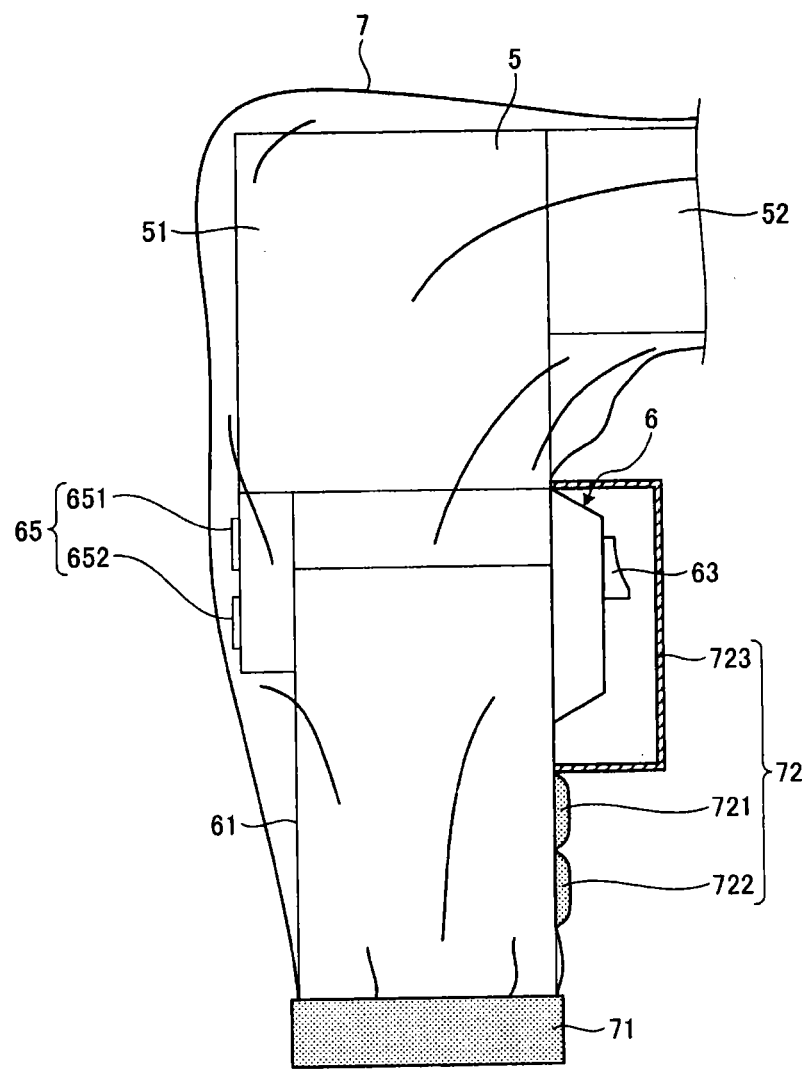
FIG. 8 is a side view seen from the direction of the arrow C of FIG. 7.

FIG. 7 is an enlarged perspective view showing a configuration of a substantial part of a sterile drape according to an embodiment 2 of the present disclosure, and a configuration of a part, to which the substantial part is applied, of a medical observation apparatus. FIG. 8 is a partially sectional side view seen from the direction (direction perpendicular to the first and second axes $O_1$ and $O_2$) of the arrow C of FIG. 7. Applied to cover the observation apparatus 2, a sterile drape 7 shown in FIGS. 7 and 8 keeps the surfaces of the observation apparatus 2 sterile.

The sterile drape 7 includes an opening cover 71 and an attaching part 72. The opening cover 71 has the same configuration as the opening cover 11 of the sterile drape 1. The main body of the sterile drape 7 is formed of a material similar to that of the main body of the sterile drape 1 in the embodiment 1.

The attaching part 72 includes two protrusions 721 and 722 and a switch cover (example of an input-part cover) 723. The protrusions 721 and 722 are provided contiguously on the outer surface of the bag-shaped main body of the sterile drape 7, and, when attached to the tubular part 61, placed on the surface of the tubular part 61 so as to locate side by side in the height direction of the tubular part 61. The switch cover 723, formed contiguously to the end part, opposite to the end part contiguous to the protrusion 722, of the protrusion 721, is provided to cover the arm operation switch 63. FIG. 8 shows a cross-section of the switch cover 723 passing through the first and second axes $O_1$ and $O_2$ shown in FIG. 7. The switch cover 723 has a thickness small enough to make the arm operation switch 63 operable through the switch cover 723.

The protrusions 721 and 722 respectively include attaching recessed portions similarly to the protrusions 121 and 122 of the sterile drape 1 described above. The attaching recessed portions are respectively fitted to the attaching protruding portions 611 and 612 (see FIG. 5) formed on the surface of the tubular part 61, thereby fixed to the tubular part 61. Note that the switch cover 723 may be configured to be fitted to the tubular part 61, too.

The attaching part 72, formed of an elastic member similar to that of the attaching part 12 in the embodiment 1, has a function of preventing slip of an object contacting from outside.

The embodiment 2 of the present disclosure as described above can provide effects similar to those of the embodiment 1. In addition, this embodiment 2, in which the attaching part 72 further includes the switch cover 723, can prevent the main body of the sterile drape 7 from slipping on the microscope part 6 while the user operates the arm operation switch 63.

Embodiment 3

Figure 9:
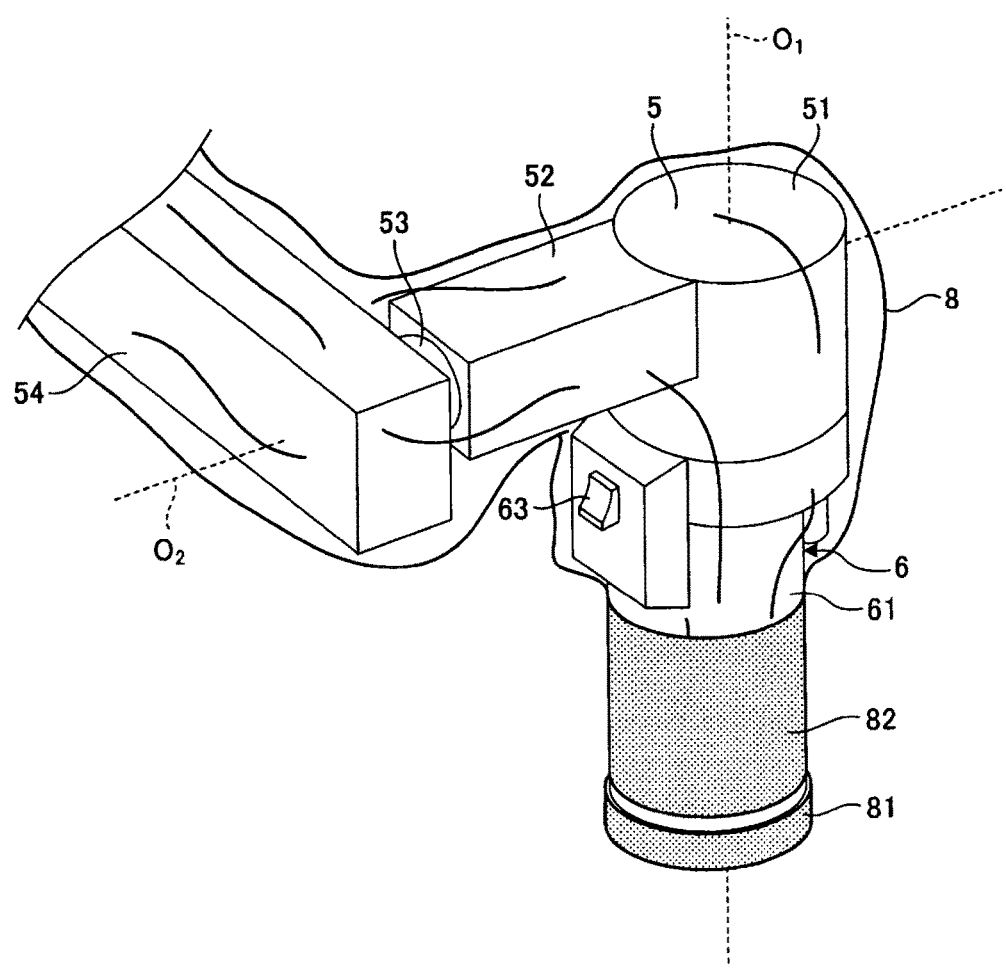
FIG. 9 is an enlarged perspective view showing a configuration of a substantial part of a sterile drape according to an embodiment 3 of the present disclosure, and a configuration of a part, to which the substantial part is applied, of a medical observation apparatus.

FIG. 9 is an enlarged perspective view showing a configuration of a substantial part of a sterile drape according to an embodiment 3 of the present disclosure, and a configuration of a part, to which the substantial part is applied, of a medical observation apparatus. Applied to cover the observation apparatus 2, a sterile drape 8 shown in FIG. 9 keeps the surfaces of the observation apparatus 2 sterile.

The sterile drape 8 includes an opening cover 81 and an attaching part 82. The opening cover 81 has the same configuration as the opening cover 11 of the sterile drape 1. The main body of the sterile drape 8 is formed of a material similar to that of the main body of the sterile drape 1 in the embodiment 1.

The attaching part 82 has a cylindrical shape whose diameter is a bit smaller than that of the tubular part 61. The attaching part 82 is fixed and attached to the tubular part 61 in a manner of encircling the tubular part 61. The attaching part 82, formed of an elastic member similar to that of the attaching part 12 in the embodiment 1, has a function of preventing slip of an object contacting from outside.

In attaching the attaching part 82 to the tubular part 61, the attaching part 82 is stretched, and then the tubular part 61 is inserted through the stretched attaching part 82 from the front end of the tubular part 61. Thereafter, the opening cover 81 is attached to the front end of the microscope part 6, so that application of the sterile drape 8 to the microscope part 6 is finished.

The embodiment 3 of the present disclosure as described above can provide effects similar to those of the embodiment 1. In addition, in this embodiment 3, the attaching part 82 is formed of a cylindrical elastic member, thus being easier to apply to the microscope part 6. Moreover, since the attaching part 82 is applied to the microscope part 6 in a manner of encircling the microscope part 6, the user can grip the microscope part 6 even more reliably and thus can operate the microscope part 6 as the user wishes.

Note that, in this embodiment 3, some input-part cover may also be provided to cover other switches that are provided on the tubular part 61 such as the magnification changing switches 64 and the focal-distance changing switches 65. Note also that the cross-section of the tubular part 61 does not have to be circular, but may be partially atypical, or alternatively some protrusions may be provided partially on the outer surface of the tubular part 61. This more effectively restrains the rotation of the attaching part 82 on the tubular part 61, and facilitates the positioning of the attaching part 82 when getting applied to the tubular part 61.

Figure 10:
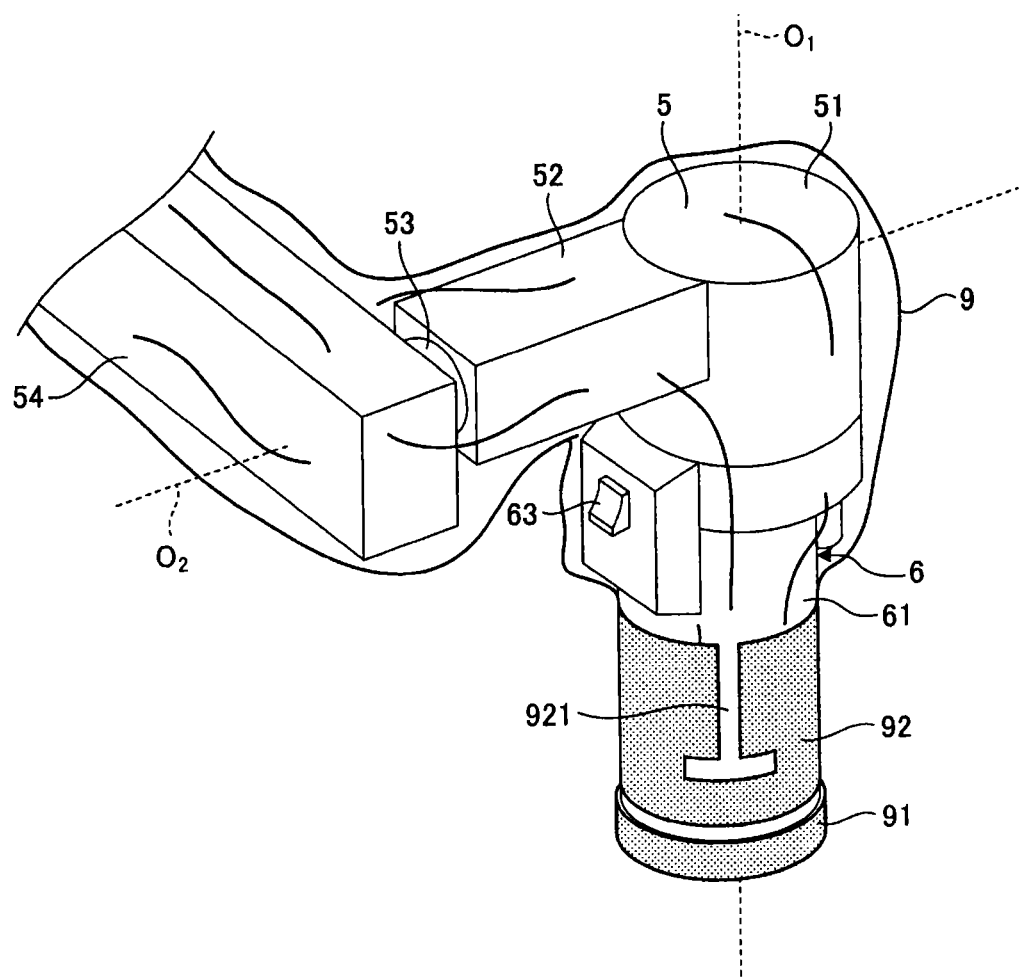
FIG. 10 is an enlarged perspective view showing a configuration of a substantial part of a sterile drape according to a modification of the embodiment 3 of the present disclosure, and a configuration of a part, to which the substantial part is applied, of a medical observation apparatus.

FIG. 10 is an enlarged perspective view showing a configuration of a substantial part of a sterile drape according to a modification of the embodiment 3, and a configuration of a part, to which the substantial part is applied, of a medical observation apparatus. A sterile drape 9 shown in FIG. 10 includes an opening cover 91 and an attaching part 92. Similarly to the attaching part 82, the attaching part 92 has a cylindrical shape whose diameter is a bit smaller than that of the tubular part 61, and is formed of a material similar to that of the attaching part 82. Note that the opening cover 91 has the same configuration as the opening cover 11 of the sterile drape 1.

The attaching part 92 is provided with a slit 921 having a T shape formed to extend partway in the height direction of its cylindrical shape from the end part, other than the end part facing the opening cover 91, of the attaching part 92.

In attaching the attaching part 92 to the microscope part 6, the tubular part 61 is inserted through the attaching part 92 from the front end of the tubular part 61 with the slit 921 opened by stretching the attaching part 92 in radial directions. Thereafter, the opening cover 91 is attached to the front end of the microscope part 6, so that application of the sterile drape 9 to the microscope part 6 is finished.

This modification, in which the slit 921 is formed in the attaching part 92, enables the attaching part 92 to be applied to the tubular part 61 with the diameter of the attaching part 92 expanded. This further facilitates the application.

Note that the number of slits 921 may alternatively be two or more. Note also that the shape of the slit is not limited to the T shape described above, but may be changed as appropriate. To prevent the mouth of the slit 921 from opening after the attaching part 92 is attached to the tubular part 61, a fix member configured to fix the mouth may additionally be provided. This enables more reliable fixation of the attaching part 92 to the tubular part 61.

Embodiment 4

Figure 11:
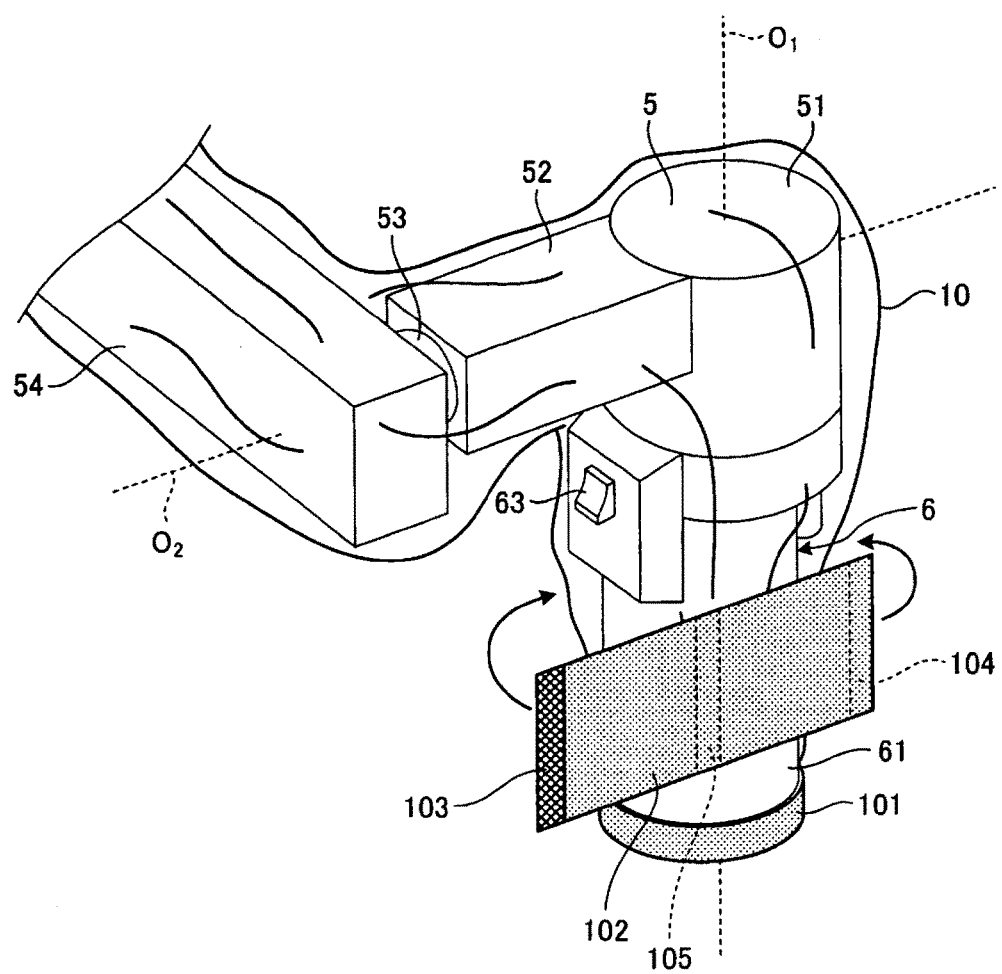
FIG. 11 is an enlarged perspective view showing a configuration of a substantial part of a sterile drape according to an embodiment 4 of the present disclosure, and a configuration of a part, to which the substantial part is applied, of a medical observation apparatus.

FIG. 11 is an enlarged perspective view showing a configuration of a substantial part of a sterile drape according to an embodiment 4 of the present disclosure, and a configuration of a part, to which the substantial part is applied, of a medical observation apparatus. Applied to cover the observation apparatus 2, a sterile drape 10 shown in FIG. 11 keeps the surfaces of the observation apparatus 2 sterile.

The sterile drape 10 includes an opening cover 101 and an attaching part 102. The opening cover 101 has the same configuration as the opening cover 11 of the sterile drape 1. The main body of the sterile drape 10 is formed of a material similar to that of the main body of the sterile drape 1 in the embodiment 1.

The attaching part 102 has a band shape, and includes engaging parts 103 and 104 respectively on both end portions in the band length direction (corresponding to the direction in which the attaching part 102 encircles the microscope part 6 when attached to the microscope part 6). The engaging parts 103 and 104, each formed of a hook-and-loop fastener, for example, are engageable with each other. A central region 105 of the attaching part 102 in the band length direction is bonded onto the outer surface of the bag-shaped main body of the sterile drape 10 so as to extend in the band width direction (corresponding to the height direction of the microscope part 6 when the attaching part 102 is attached to the microscope part 6). The band length of the attaching part 102, except for portions overlapped with each other by the engagement of the engaging parts 103 and 104, is a bit smaller than the outer perimeter of the tubular part 61.

In attaching the sterile drape 10 to the tubular part 61 from the state shown in FIG. 11, the attaching part 102 is wrapped around the tubular part 61 so as to overlap the both ends with each other, and then the engaging parts 103 and 104 are engaged with each other, so that the attaching part 102 is fixed to the tubular part 61.

The attaching part 102, formed of an elastic member similar to that of the attaching part 12 in the embodiment 1, has a function of preventing slip of an object contacting from outside.

The embodiment 4 of the present disclosure as described above can provide effects similar to those of the embodiment 1. In addition, in this embodiment 4, the attaching part 102 is easier to apply to the microscope part 6. Moreover, since the attaching part 102 encircles the microscope part 6, the user can grip the microscope part 6 even more reliably and thus can operate the microscope part 6 as the user wishes.

Furthermore, in this embodiment 4, the attaching part 102 has a thin band shape before being attached to the microscope part 6. This prevents the attaching part 102 from being bulky, and also eliminates the possibility of defects of the attaching part 102 such as deformation serious enough to make the attachment to the microscope part 6 difficult. Thus, the sterile drape 10 is easy to pack and highly storage-efficient in a package at the time of shipment, as well as being inexpensive and economical.

Note that, in this embodiment 4, the cross-section of the tubular part 61 does not have to be circular, but may be partially atypical, or alternatively some protrusions may be provided partially on the outer surface of the tubular part 61. This more effectively restrains the rotation of the attaching part 102 on the tubular part 61, and facilitates the positioning of the attaching part 102 when getting applied to the tubular part 61. Even if the tubular part 61 has an atypical shape as described above, the attaching part 102, configured to be applied to the tubular part 61 by being wrapped therearound, can be easily fitted to the tubular part 61.

Embodiment 5

Figure 12:
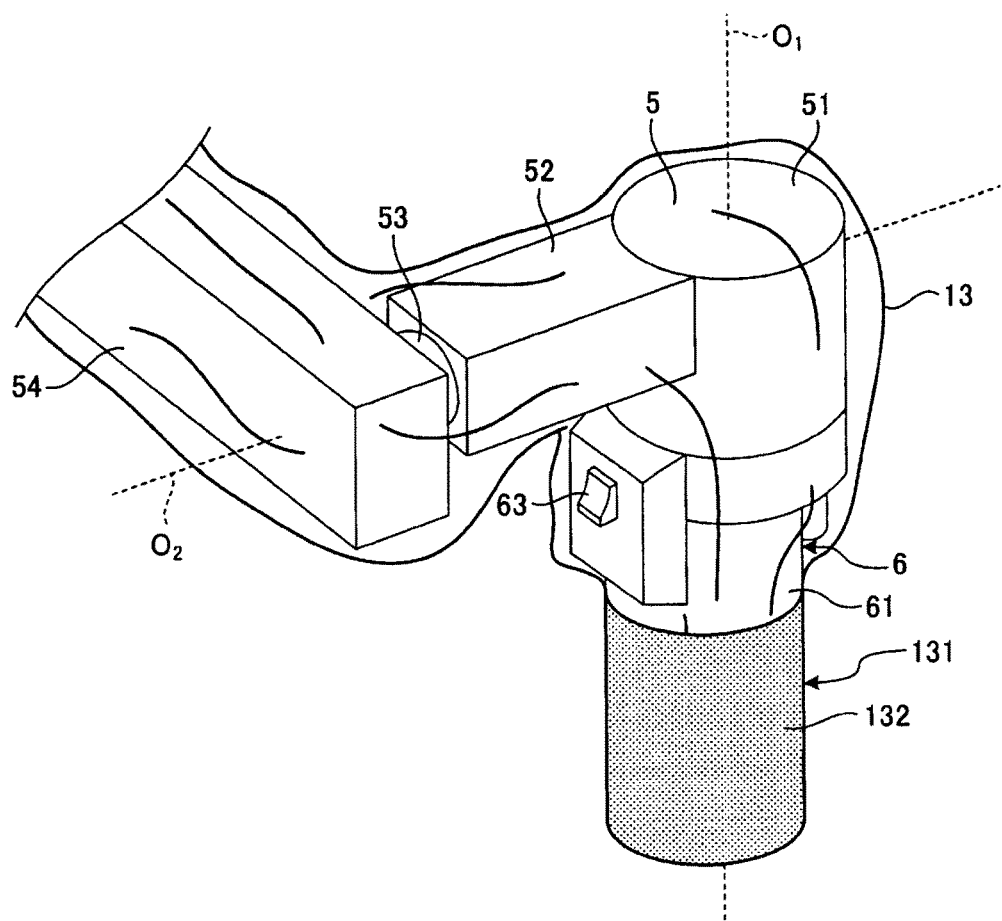
FIG. 12 is an enlarged perspective view showing a configuration of a substantial part of a sterile drape according to an embodiment 5 of the present disclosure, and a configuration of a part, to which the substantial part is applied, of a medical observation apparatus.
Figure 13:
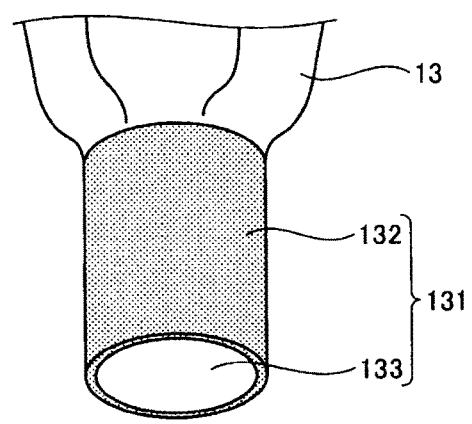
FIG. 13 is a view, seen from the direction different from that of FIG. 12, of the configuration of the substantial part of the sterile drape according to the embodiment 5 of the present disclosure.

FIG. 12 is an enlarged perspective view showing a configuration of a substantial part of a sterile drape according to an embodiment 5 of the present disclosure, and a configuration of a part, to which the substantial part is applied, of a medical observation apparatus. FIG. 13 is a view of the substantial part of the sterile drape according to the embodiment 5 seen from the direction different from that of FIG. 12. Applied to cover the observation apparatus 2, a sterile drape 13 shown in FIGS. 12 and 13 keeps the surfaces of the observation apparatus 2 sterile. The main body of the sterile drape 13 is formed of a material similar to that of the main body of the sterile drape 1 in the embodiment 1.

The sterile drape 13 includes an attaching part 131 configured to be fixed and attached to a front end of the microscope part 6 and having a function of preventing slipping on the tubular part 61. The attaching part 131 includes a tubular part 132 and a cover glass 133. The tubular part 132 formed of an elastic member has a cylindrical shape whose diameter is smaller than the outer diameter of the microscope part 6. The cover glass 133 provided to an end part of the tubular part 132 in the height direction thereof, protects the opening surface through which the microscope part 6 condenses light from the observation object, the end part corresponding to the front end of the microscope part 6. The attaching part 131, formed of an elastic member similar to that of the attaching part 12 in the embodiment 1, has a function of preventing slip of an object contacting from outside.

In attaching the attaching part 131 to the microscope part 6, the tubular part 61 is inserted through the attaching part 131 from the front end of the tubular part 61 by stretching, in radial directions, the end part, other than the end part provided with the cover glass 133, of the attaching part 131. Thereafter, the cover glass 133 is applied in alignment with the front end of the microscope part 6, so that application of the sterile drape 13 to the microscope part 6 is finished.

The embodiment 5 of the present disclosure as described above can provide effects similar to those of the embodiment 1. In addition, in this embodiment 5, the attaching part 131 functions also as an opening cover, which saves the effort of applying, in addition to the attaching part, an independent opening cover to the microscope part 6.

Note that a slit similar to the T-shaped slit 921 (see FIG. 10) described in the modification of the embodiment 3 may be formed in the attaching part 131.

Figure 14:
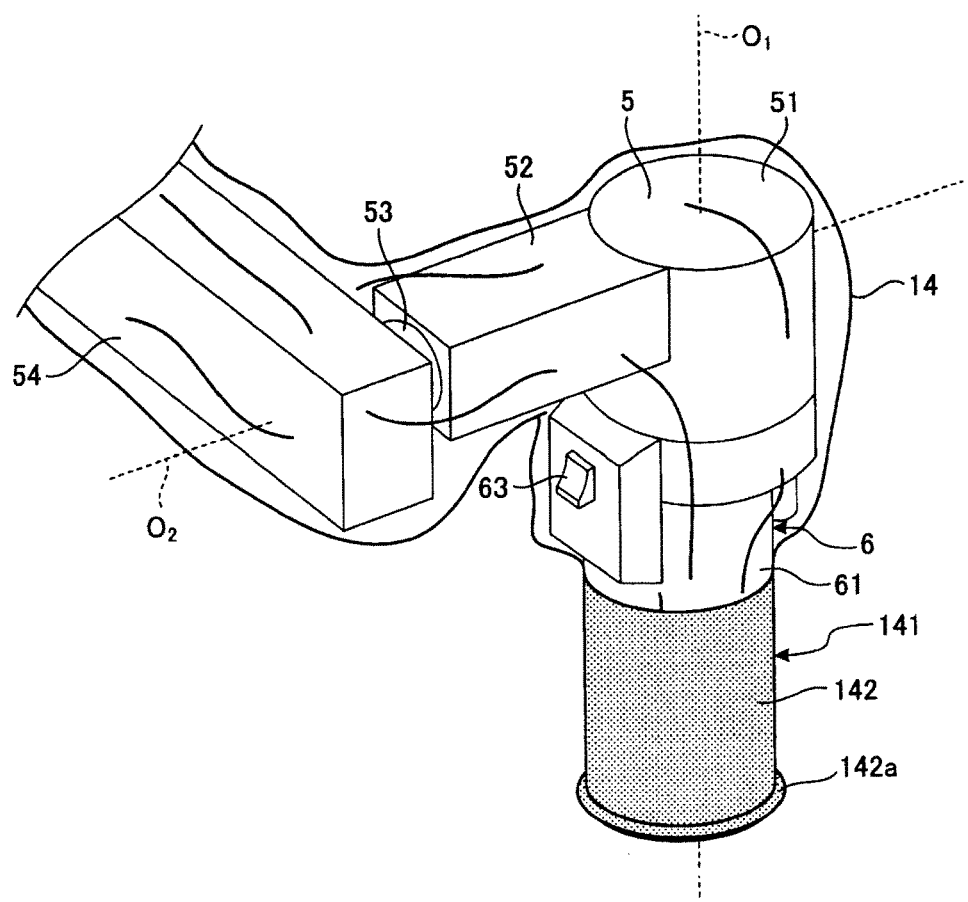
FIG. 14 is an enlarged perspective view showing a configuration of a substantial part of a sterile drape according to a modification of the embodiment 5 of the present disclosure, and a configuration of a part, to which the substantial part is applied, of a medical observation apparatus.
Figure 15:
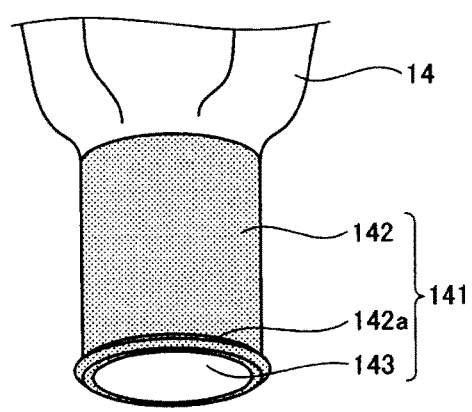
FIG. 15 is a view, seen from the direction different from that of FIG. 14, of the configuration of the substantial part of the sterile drape according to the modification of the embodiment 5 of the present disclosure.

FIG. 14 is an enlarged perspective view showing a configuration of a substantial part of a sterile drape according to a modification of the embodiment 5, and a configuration of a part, to which the substantial part is applied, of a medical observation apparatus. FIG. 15 is a view of the substantial part of the sterile drape according to this modification seen from the direction different from that of FIG. 14. The sterile drape 14 shown in FIGS. 14 and 15 includes an attaching part 141 configured to be attached to the front end of the microscope part 6.

The attaching part 141 includes a tubular part 142 and a cover glass 143. The tubular part 142, formed of an elastic member, has a cylindrical shape whose diameter is smaller than the outer diameter of the microscope part 6. The cover glass 143, provided to one end part, corresponding to the front end of the microscope part 6, of the end parts of the tubular part 142 in the height direction thereof, protects the opening surface of the microscope part 6.

The tubular part 142 has a flange portion 142a protruding in radial directions at an outer periphery portion of the cover glass 143. The tubular part 142, formed of an elastic member similar to that of the attaching part 12 in the embodiment 1, has a function of preventing slip of an object contacting from outside.

This modification, in which the flange portion 142a is formed, prevents the user from accidentally touching the opening cover in gripping the microscope part 6, thereby from tainting the opening cover or from blocking the optical path of illumination light or observation light. In addition, in this modification, where to grip the microscope part 6 can be physically restricted, so that the user can grip the microscope part 6 constantly with uniform sensitivity, and thus can stably operate the microscope part 6.

Other Embodiments

Hereinabove, the modes for carrying out the present disclosure has been described, but the present disclosure should not be limited only to the embodiments 1 to 5. For example, stretchable looseness prevention members each having a ring shape may additionally be placed on the main body of the sterile drape, as appropriate. Example configurations of the looseness prevention member may include configurations similar to those of the attaching part 82 shown in FIG. 9, the attaching part 92 shown in FIG. 10 and the attaching part 102 shown in FIG. 11.

Each looseness prevention member is preferably provided to a portion, prone to loose in accordance with the movement of the support part 5, of the sterile drape. Examples of such portions may include a portion around each joint part of the support part 5.

An embodiment of the present disclosure may be applied to a microscope having, like surgery microscopes in the past, one or more grip parts which are located separately from the lens barrel and which have various switches formed thereon.

As described above, the present disclosure may include various embodiments and the like within the technical ideas described in the scope of claims.

It should be understood by those skilled in the art that various modifications, combinations, sub-combinations and alterations may occur depending on design requirements and other factors insofar as they are within the scope of the appended claims or the equivalents thereof.

What is claimed is:

1. A sterile drape configured to cover a medical observation apparatus to keep the medical observation apparatus sterile, the medical observation apparatus including
    a microscope part configured to magnify and image a microfine site of an observation object,
    an input part configured to receive an input of an operation instruction to the microscope part, and
    a grip part having a bar shape and having a surface provided with at least a portion of the input part,
    the sterile drape comprising:
        an attaching part configured to be fixed to the grip part in a state where the sterile drape covers the medical observation apparatus,
        wherein the attaching part includes a sheet-shaped band and is further configured to be fixed to the grip part with the sheet-shaped band,
        wherein the grip part is an tubular part of the microscope part which is disposed below the input part, and wherein the medical observation apparatus is connected to a display that display the image of the microfine site of the observation object.

2. The sterile drape according to claim 1, further comprising:

an input-part cover formed of an elastic member and configured to cover the at least a portion of the input part provided to the grip part in the state where the sterile drape covers the medical observation apparatus.

3. The sterile drape according to claim 1, wherein the microscope part of the medical observation apparatus has a pillar shape to function as the grip part, and wherein the attaching part is configured to be fixed to the microscope part.

4. The sterile drape according to claim 1, wherein the attaching part has a shape fittable to a surface of the grip part.

5. The sterile drape according to claim 1, wherein the attaching part has a band shape, and includes engaging parts respectively on both end portions in a band length direction in a manner that one of the end portions is engaged with the other end portion.

6. The sterile drape according to claim 5, wherein the attaching part is formed of an elastic member.

7. The sterile drape according to claim 1, wherein the microscope part of the medical observation apparatus has a pillar shape to function as the grip part, wherein the medical observation apparatus further includes a support part having at least one set of two arm parts and a joint part that rotatably connects one of the two arm parts to the other, and supporting the microscope part at a front end part rotatably around an axis in a height direction of the microscope part, and an arm operation switch provided to a side surface of the microscope part, and configured to receive an operation input for allowing rotations of the arm parts, the side surface corresponding to an upper side of an image based on an imaging signal, and wherein the input part includes the arm operation switch.

8. The sterile drape according to claim 1, wherein the sheet-shaped band of the attaching part includes engaging parts respectively on both end portions in the band length direction, the engaging parts being engageable with each other.

9. The sterile drape according to claim 1, wherein the sheet-shaped band of the attaching part is an elastic sheet-shaped band.

10. The sterile drape according to claim 1, wherein the tubular part is at a distal end of the medical observation apparatus closest to the observation object.

* * * * *